United States Patent [19]
Kohno et al.

[11] Patent Number: 6,132,719
[45] Date of Patent: Oct. 17, 2000

[54] MONOCLONAL ANTIBODY AND METHOD OF IMMUNOLOGICAL ANALYSIS OF E-D-DIMER AND E-DD/E COMPLEX

[75] Inventors: Isao Kohno; Kimiko Inuzuka; Yumiko Ito; Ken Fukushi, all of Tokyo, Japan

[73] Assignee: Iatron Laboratories, Inc., Tokyo, Japan

[21] Appl. No.: 08/983,047

[22] PCT Filed: May 15, 1997

[86] PCT No.: PCT/JP97/01639

§ 371 Date: Jan. 15, 1998

§ 102(e) Date: Jan. 15, 1998

[87] PCT Pub. No.: WO97/43315

PCT Pub. Date: Nov. 20, 1997

[30] Foreign Application Priority Data

May 15, 1996 [JP] Japan ................................ 8-145139

[51] Int. Cl.[7] .................... A61K 39/395; G01N 33/53

[52] U.S. Cl. .................................. 424/139.1; 424/141.1; 435/7.1

[58] Field of Search .............................. 424/139.1, 141.1, 424/145.1, 158.1; 435/7.1, 346; 530/300

*Primary Examiner*—Elizabeth Kemmerer
*Assistant Examiner*—Nirmal S. Basi
*Attorney, Agent, or Firm*—Sughrue, Mion, Zinn, Macpeak & Seas, PLLC

[57] ABSTRACT

A monoclonal antibody which specifically reacts with D-monomer produced by digesting human fibrinogen with granulocyte elastase and D-domain containing digestion products produced by digesting human stabilized fibrin with granulocyte elastase, but does not react with fibrinogen, or fragment X, Y or E produced by digesting fibrinogen with granulocyte elastase is disclosed. The D-dimer or DD/E complex produced by digestion with granulocyte elastase in a sample from a living body can be analyzed without being interferred with fibrinogen, digestion products of fibrinogen with plasmin, or digestion products of stabilized fibrin with plasmin, using the monoclonal antibody.

9 Claims, 1 Drawing Sheet

F I G. 1
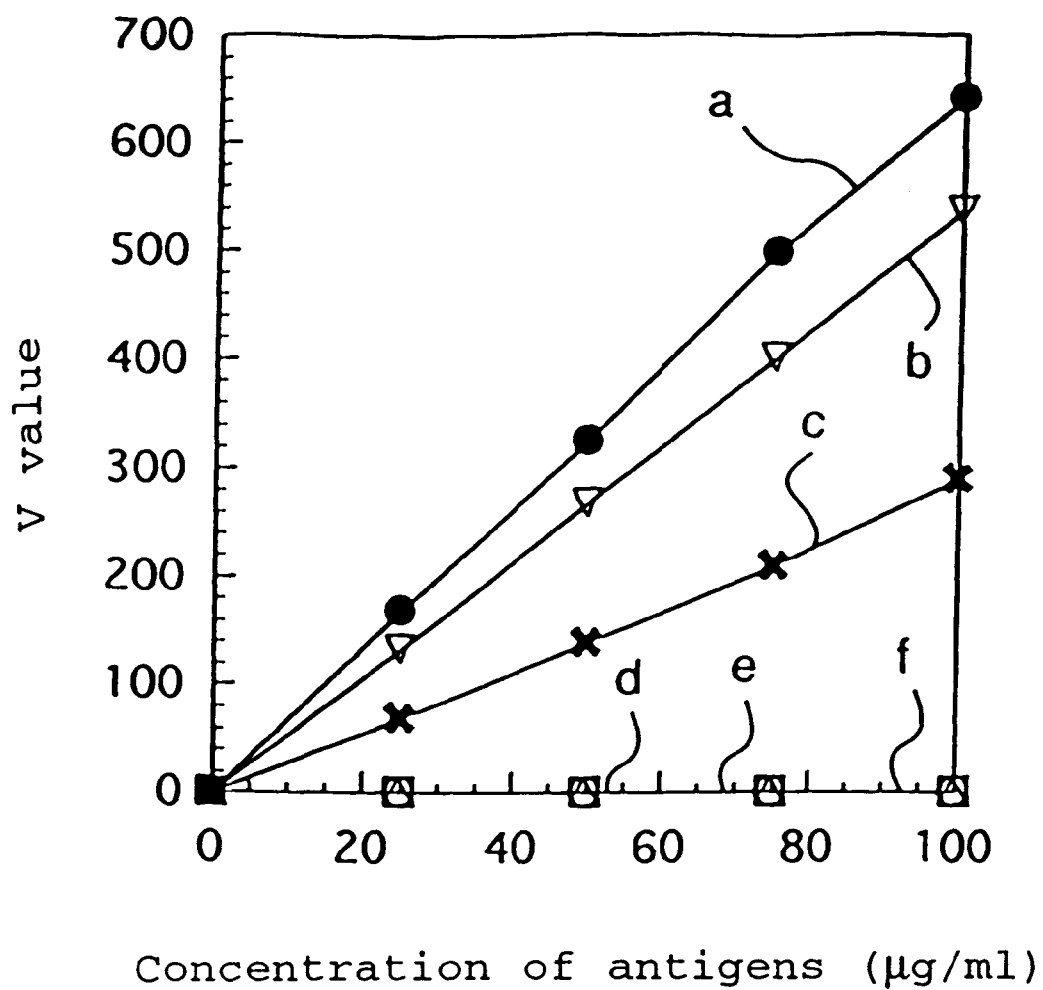

MONOCLONAL ANTIBODY AND METHOD OF IMMUNOLOGICAL ANALYSIS OF E-D-DIMER AND E-DD/E COMPLEX

This application is a National Stage Entry of PCT/JP97/01639 filed May 15, 1997, in turn claiming benefit under 35 U.S.C. § 119 to Japanese application 8-145139, filed May 15, 1996.

TECHNICAL FIELD

The present invention relates to a novel monoclonal antibody, and an immunological assay of a D-dimer produced by digesting human stabilized fibrin with granulocyte elastase (hereinafter sometimes referred to as "e-D-dimer") and a DD/E complex produced by digesting human stabilized fibrin with granulocyte elastase (hereinafter sometimes referred to as e-DD/E complex).

The monoclonal antibody according to the present invention is useful as a reagent for the immunological assay of the e-D-dimer and the e-DD/E complex which are produced in plasma or serum when human stabilized fibrin is digested with granulocyte elastase. The e-D-dimer and the e-DD/E complex are useful as a maker to predict postoperative disorder of multiple organs and pulmonary emphysema.

BACKGROUND ART

Digestion products of human stabilized fibrin with various proteases are useful as diagnostic markers in clinical diagnosis. For example, a D-dimer produced by digesting human stabilized fibrin with plasmin (hereinafter sometimes referred to as "p-D-dimer") and a DD/E complex produced by digesting human stabilized fibrin with plasmin (hereinafter sometimes referred to as "p-DD/E complex") are widely used as a diagnostic marker of disseminated intravascular coagulation (DIC). In determination of the p-D-dimer and p-DD/E complex in a sample from a living body, agglutination of latex sensitized with a monoclonal antibody specific to the p-D-dimer is generally used.

Further, the e-D-dimer and e-DD/E complex of human stabilized fibrin are useful as a marker to predict postoperative disorder of multiple organs and pulmonary emphysema. Agglutination reaction of latex sensitized with the above monoclonal antibody specific to the p-D-dimer makes it possible to determine the p-D-dimer and p-DD/E complex produced by the action of plasmin, but does not make it possible to determine the e-D-dimer and e-DD/E complex produced by the action of granulocyte elastase. Therefore, there have been some attempts to determine the e-D-dimer and e-DD/E complex of human stabilized fibrin.

A monoclonal antibody which reacts with an N-terminal site (Aα22-36) newly formed on the Aa chain of fibrinogen when it is digested with granulocyte elastase was reported (Blood Coagulation and Fibrinolysis, vol. 6, p 259, 1995). The monoclonal antibody has an antigen-binding site in an E domain, and therefore, different from the monoclonal antibody according to the present invention. Further, the former monoclonal antibody slightly reacts with fibrinogen, and thus, digestion products of fibrinogen or fibrin with granulocyte elastase in plasma cannot be determined by EIA wherein the former monoclonal antibody is used.

Further, polyclonal antibodies prepared by adsorbing and removing antibodies which can react with plasmin-digested D-monomer, plasmin-digested D-dimer, plasmin-digested DD/E complex and fibrinogen from polyclonal antibodies obtained by immunization with granulocyte elastase-D-fragment of fibrinogen (J. Lab. Clin. Med. vol. 102, p 858, 1983) are sometimes used, but the procedure is cumbersome.

DISCLOSURE OF INVENTION

The object of the present invention is to provide an assay method of an amount of the e-D-dimer and e-DD/E complex in a sample from a living body, such as plasma, without an influence of amounts of fibrinogen, plasmin-digested products of fibrinogen, or plasmin-digested products of human stabilized fibrin (particularly, p-D-dimer or p-DD/E complex) which are expected to co-exist therewith in the sample.

Other objects and advantages will be apparent from the following description.

According to the present invention, there is provided a monoclonal antibody which specifically reacts with a D-monomer produced by digesting human fibrinogen with granulocyte elastase and D-domain containing digestion products produced by digesting human stabilized fibrin with granulocyte elastase, but does not react with fibrinogen, or a fragment X, Y or E produced by digesting fibrinogen with granulocyte elastase.

According to the present invention, there is also provided a monoclonal antibody which reacts with a peptide having an amino acid sequence, SEQ ID NO: 1:

Ser Glu Asp Leu Arg Ser.

Further, according to the present invention, there is provided an immunological assay for a D-dimer and a DD/E complex which are produced by digesting human stabilized fibrin with granulocyte elastase, in a sample from a living body, characterized by bring the sample into contact with a carrier coated with the above monoclonal antibodies or fragments thereof, and detecting aggregate formed by the D-dimer or DD/E complex with the coated carrier.

BRIEF DESCRIPTION OF DRAWINGS

FIG. 1 is a graph illustrating correlation between concentrations of antigens and agglutination rates, in agglutination reaction caused by contacting various antigens with latexes sensitized with monoclonal antibody IF-101 of the present invention.

BEST MODE FOR CARRYING OUT THE INVENTION

The term "granulocyte elastase" used herein means elastase which is contained in an azurophil granule of granulocyte; released from granulocyte activated by local inflammation; and hydrolyzes physiological substrates, for example, elastin, collagen, fibronectin or proteoglycan contained in cellular matrix, or blood proteins, such as fibrinogen, fibrin, plasminogen or antithrombin III, at the carboxylic acid terminus of hydrophobic amino acids, such as valine or alanine.

In the present specification, a digested product formed by digestion with granulocyte elastase is sometimes denoted by placing the symbol "e-" in front of the product. For example, the D-monomer produced by digesting human fibrinogen with granulocyte elastase, a fragment X produced by digesting human fibrinogen with granulocyte elastase, a fragment Y produced by digesting human fibrinogen with granulocyte elastase, or a fragment E produced by digesting human fibrinogen with granulocyte elastase is denoted by an e-D-monomer of human fibrinogen, an e-fragment X of human fibrinogen, an e-fragment Y of human fibrinogen, or an e-fragment E of human fibrinogen, respectively.

Further, in the present specification, a digested product formed by digestion with plasmin is sometimes denoted by placing the symbol "p-" in front of the product.

The monoclonal antibody of the present invention may be obtained by a method for producing a monoclonal antibody from a hybridoma prepared by a cell fusion method recently used in various fields.

The monoclonal antibody of the present invention specifically reacts with the D-monomer produced by digesting human fibrinogen with granulocyte elastase (e-D-monomer) and the D-domain-containing digestion products produced by digesting human stabilized fibrin with granulocyte elastase, but does not react with fibrinogen, or the fragment X, Y or E produced by digesting fibrinogen with granulocyte elastase. The term "D-domain containing digestion products produced by digesting human stabilized fibrin with granulocyte elastase" means digestion products which is produced by treating human stabilized fibrin with granulocyte elastase, and contain an e-D-domain of human stabilized fibrin. For example, there may be mentioned e-DD/E polymer-like substances containing e-DD/E base units, the e-D-dimer, or the e-DD/E complex, particularly the e-D-dimer, or the e-DD/E complex.

Preferable monoclonal antibody of the present invention does not react with digestion products of human fibrinogen with plasmin, or digestion products of human stabilized fibrin with plasmin.

The present invention relates to a monoclonal antibody which reacts with a peptide having an amino acid sequence, SEQ ID NO: 1:

Ser Glu Asp Leu Arg Ser.

The above amino acid sequence of SEQ ID NO: 1 corresponds to the amino acid sequence of the 112nd amino acid to 117th amino acid in the Aα chain, counting from the N-terminus of the Aα chain. The Aα chain is one of three polypeptides (i.e., Aα chain, Bβ chain and γ chain) which human fibrinogen is composed of. Further, the above amino acid sequence of SEQ ID NO: 1 corresponds to the amino acid sequence of the first amino acid to the sixth amino acid of an Aα chain partial fragment, counting from the amino group-terminus of the Aα chain partial fragment which is one of polypeptides composing granulocyte elastase-digested D-monomers of human fibrinogen; namely, a peptide produced by removing a polypeptide having an amino acid sequence of the first to 111th amino acids from the Aα chain; hereinafter referred to as /α chain).

Preferable monoclonal antibody of the present invention reacts with the peptide having the amino acid sequence of SEQ ID NO: 1, and specifically reacts with the e-D-monomer of human fibrinogen and the D-domain-containing digestion products of human stabilized fibrin with granulocyte elastase, but does not react with fibrinogen, or the fragment X, Y or E produced by digesting fibrinogen with granulocyte elastase. More preferable monoclonal antibody of the present invention does not react with the digestion products of human fibrinogen with plasmin, or the digestion products of human stabilized fibrin with plasmin.

The monoclonal antibody of the present invention can be produced by culturing a hybridoma (such as a mouse hybridoma) capable of producing such a monoclonal antibody, for example, in a suitable medium or abdominal cavity in a mammal, such as a mouse. The hybridoma can be produced by cell fusion of a spleen cell from a mammal (such as a mouse) or a bird immunized with the e-D-dimer as an immunogen and a melanoma cell of a mammal (such as a mouse) in accordance with the standard method of the cell fusion by Köhler and Milstein (see Nature, vol. 256, p 495, 1975). More particularly, the hybridoma can be produced by the procedure in Examples as mentioned below.

As the medium for cultivating the hybridomas, any medium suitable for cultivation of a hybridoma may be used. Preferably, a medium comprising the Dulbeccos modified Eeagle's minimum essential medium (hereinafter referred to as DME), and fetal calf serum, L-glutamin, L-pyruvic acid and antibiotics (penicillin G and streptomycin) is used.

The cultivation of the hybridoma is preferably carried out, for example, in 5% $CO_2$ and at 37° C. for about 3 days in a medium, or for about 14 days in the abdominal cavities of mice.

It is possible to isolate or purify the monoclonal antibody of the present invention from the resulting culture liquid or mouse ascites, using, for example, a method generally applied for the isolation and purification of proteins. As examples thereof, there may be mentioned the ammonium sulfate salting out, ion exchange column chromatography using ion exchange cellulose, molecular sieve column chromatography using molecular sieve gel, affinity column chromatography using protein A binding polysaccharides, dialysis, lyophilization, or the like.

As the antibody fragment of the present invention, namely the antibody fragment of the monoclonal antibody according to the present invention which contains an antigen-binding site specifically reacting with the D-monomer produced by digesting human fibrinogen with granulocyte elastase and the D-domain-containing digestion products produced by digesting human stabilized fibrin with granulocyte elastase, there may be mentioned, for example, Fab, Fab', $F(ab')_2$, Fv or the like. The fragment may be obtained, for example, by digesting the monoclonal antibody of the present invention with a protease in a conventional method, and then carrying out a conventional isolation and purification method of proteins.

The assay of the present invention can be applied to a conventional agglutination method, such as a latex agglutination method, except that the monoclonal antibody or the fragment thereof according to the present invention is used. The assay of the present invention can be applied not only to a visual detection of agglutination on a slide glass, but also to an optically automatic assay by an automatic analyzer. Further, according to the assay of the present invention, it is possible to detect the presence of the granulocyte elastase-digested D-dimer and the granulocyte elastase-digested DD/E complex of human stabilized fibrin, or semi-quantitatively or quantitatively determine the granulocyte elastase-digested D-dimer and the granulocyte elastase-digested DD/E complex of human stabilized fibrin.

A carrier on which the monoclonal antibodies and/or the fragments thereof are coated and which may be used in the assay of the present invention can be prepared by a conventionally known method. For example, a carrier (such as water-insoluble carrier, particularly polystyrene latex) is mixed with a buffer containing the antibodies with stirring, the mixture is centrifuged, and a resulting precipitate is suspended in a suitable buffer.

The coated carrier can react with the e-D-dimer and the e-DD/E complex, and the e-D-monomer, respectively, but cannot react with other substances. When the coated carrier is brought into contact with the e-D-dimer or the e-DD/E complex, agglutination reaction of the coated carriers is caused, because the e-D-dimer and the e-DD/E complex have plural antigenic determinants. On the contrary, the e-D-monomer has only one antigenic determinant. Therefore, if the coated carrier is brought into contact with the e-D-monomer, agglutination reaction of the coated carriers is not caused. Therefore, when a sample containing the e-D-dimer, the e-DD/E complex and the e-D-monomer is brought into contact with the coated carriers, the agglutination reaction is caused by the reaction with the e-D-dimer and the e-DD/E complex. The amount of the e-D-dimer and/or the e-DD/E complex in the sample from a living body can be measured without an influence of the e-D-monomer, on the basis of the differences of such agglutination reaction.

For example, an amount of a fraction retaining a stereostructure of the e-D-dimer and/or the e-DD/E complex in the sample from a living body can be determined by mixing a certain amount of the coated latexes and a certain amount of the sample from a living body on a slide plate or a microtiter plate for a certain period of time, and observing the presence or absence of the aggregates, or the strength of the aggregates. Alternatively, an amount of a fraction retaining a stereostructure of the e-D-dimer and/or the e-DD/E complex in the sample from a living body can be determined by mixing a certain amount of the coated latexes and a certain amount of the sample from a living body, and spectroscopically measuring an increase of absorption at an appropriate wave length after a certain period of time.

Further, in the assay of the present invention, the coated carrier do not react with human fibrinogen, plasmin-digested products of human fibrinogen, or plasmin-digested products of human stabilized fibrin, even if the sample from a living body contains such compounds. Therefore, the amount of the e-D-dimer and/or the e-DD/E complex in the sample can be measured without influence of such compounds.

The sample from a living body which can be assayed in the present invention is, for example, plasma, serum, urine, or the like.

EXAMPLE

The present invention now will be further illustrated by, but is by no means limited to, the following examples.

Example 1

Preparation of e-D-Dimer and e-DD/E Complex

The e-D-dimer was prepared in accordance with, mainly, the method of Stephanie A. Olexa and Andrei Z. Budzynski (1978), the method of Olexa et al., Circulation, Suppl. 58, 119, (1979), and the method of Biochim. Biophys. Acta 576, 39 to 50. To 20 mg (10 mg/ml) of fibrinogen (Kabi Diagnostica; Sweden), human thrombin (at the final concentration of 10 units/ml) and calcium chloride (in the final concentration of 10 mM) were added, and reacted at 37° C. for 2 hours to convent fibrinogen to fibrin. Fibrin was separated from non-coagulated substances by centrifugation (18000×g) for 30 minutes. Fibrin was suspended in 20 ml of 0.15 M tris-HCl buffer (pH 7.8)/5 mM calcium chloride/0.02% $NaN_3$. To the resulting suspension, 0.5 ml of human granulocyte elastase (25 units/ml; Elastin Product; USA). Reaction was performed at 37° C. After 8 hours, diisopropyl fluorophosphate (DFP) (Mobay Chemical Corp.) was added in the final concentration of 2 mM to cease the digestion. The digestion products obtained by the treatment for 1 hour after the addition of DFP was referred to as the DD/E complex/granulocyte elastase-digested products of stabilized fibrin. The fragment was the mixture of DD/E and DD/E polymer-like substances containing DD/E base units.

The resulting DD/E complex/granulocyte elastase-digested products of stabilized fibrin was charged into Sepharose CL6B column (Pharmacia; Sweden; diameter=2.6 cm; length=90 cm) which had been equilibrated with 50 mM tris-HCl buffer (pH 7.5)/0.15 M sodium chloride/5 mM calcium chloride (hereinafter referred to as solution A), and treated by molecular sieve chromatography while developed with the solution A. The fraction of e-DD/E complex was identified and isolated by molecular weight markers, and the Ouchterlony method, using anti-D-antiserum, and anti-E-antiserum (Hoechst, Germany). The resulting e-DD/E complex was incubated at 37° C. for 4 hours in 3 M urea/50 mM citrate solution (pH 5.5). The resulting urea-treated e-DD/E complex was charged into Sepharose CL6B column (diameter=2.6 cm; length=90 cm) which had been equilibrated with 50 mM tris-HCl buffer (pH 7.4)/28 mM sodium citrate/0.1 M sodium chloride (hereinafter referred to as solution B), and developed with the solution B. The e-D-dimer (DD) fraction and the e-E (E) fraction were identified and isolated by molecular weight markers, and the Ouchterlony method, using anti-D-antiserum, and anti-E-antiserum. As a result, 10 ml of the e-D-dimer having the particular absorbance (A280 nm=2.0) was obtained. The resulting e-D-dimer was used as an immunogen for producing hybridomas which can secrete monoclonal antibodies reacting specifically to the e-D-dimer, and as an antigen for selecting the hybridomas in enzyme immunoassay (ELISA).

Example 2

Production of Hybridomas (a) Preparation of Immunized Spleen Cells

The e-D-dimer immunogen solution (A280 nm=2.0) obtained in Example 1 was mixed with an equal volume of complete Freund's adjuvant until emulsified, and then, 100 μl of the mixture was administered intraperitoneally in mice to immunize the same (first immunization). After 30 days, the above-mentioned mixture was administered intraperitoneally to the mice in the same manner (second immunization). After 21 days from the second immunization, 100 μl of the diluted solution prepared by diluting the e-D-dimer immunogen solution (A280 nm=2.0) with an equal volume of a physiological saline was administered intravenously to the mice (final immunization). After 3 days from the final immunization, the spleens were removed aseptically from the mice and used in the following cell fusion.

(b) Cell Fusion

The above-mentioned spleens aseptically taken were placed in a laboratory dish containing 5 ml of a DME medium containing 10 to 15% fetal calf serum. Then, the spleens were perfused with about 15 ml of a DME medium containing 10 to 15% fetal calf serum to flush out the spleen cells. The resulting suspension of the spleen cells was passed through a nylon mesh. The spleen cells were collected in a 50 ml centrifugation tube and were centrifuged at 500×g for 10 minutes. To the resulting pellets, 3 to 5 ml of a hemolyzing solution (155 mM $NH_4Cl$, 10 mM $KHCO_3$, 1 mM $Na_2EDTA$; pH 7.0) was added to suspend the pellets. The suspension was allowed to stand at 0° C. for 5 to 10 minutes to lyse the red blood cells therein. A DME medium (10 to 20 ml) containing 10 to 15% fetal calf serum was added, and the mixture was centrifuged. The resulting cell pellets were washed with a DME medium by the centrifugation method and the number of living spleen cells was counted.

The above spleen cells ($1\times10^8$) were added to about $2\times10^7$ pre-cultivated mouse myeloma cells SP2/0-Ag14 and the whole was thoroughly mixed in a DME medium, and centrifuged (500×g, 10 minutes). The supernatant was sucked up, and the pellets were thoroughly unfastened. 0.5 ml of 40% polyethylene glycol 4000 solution (warmed at 37° C.) was added dropwise, and then, the centrifugation tube was gently rotated by hand for 1 minute to thereby mix the polyethylene glycol solution with the cell pellets. Then, a DME medium warmed at 37° C. was added in 1 ml amounts every 30 seconds and the tube was gently rotated.

After this procedure was repeated 10 times, 20 to 30 ml of a DME medium containing 10 to 15% fetal calf serum was added and the whole was centrifuged (500×g, 10 minutes). After the supernatant was removed, the cell pellets were washed twice by the centrifugation method with a HAT medium (prepared by adding, to a DME medium, aminopterin, thymidine and hypoxanthine so that the concentrations thereof became to $4 \times 10^{-7}$ M, $1.6 \times 10^{-5}$ M, and $1 \times 10^{-4}$ M, respectively) containing 10 to 15% fetal calf serum, and then suspended in 40 ml of the HAT medium. The cell suspension was poured into each well of 96-well cell cultivation plates in an amount of 200 µl/well, and cultivated in a carbon dioxide gas incubator containing 5% carbon dioxide gas at 37° C. During the cultivation, about 100 µl of the medium was removed from each of the wells at 2 to 3 day intervals and 100 µl of fresh HAT medium was added to select the hybridomas which grew in the HAT medium. After about 8 days, the medium was substituted for an HT medium (prepared by adding, to a CME medium, thymidine and hypoxanthine so that the concentrations thereof became to $1.6 \times 10^{-5}$ M and $1 \times 10^{-4}$ M, respectively) containing 10 to 15% fetal calf serum and the growth of the hybridomas was observed. Around the tenth day, the hybridomas producing the antibodies reactindimer (heremonomer and e-D-dimer (hereinafter referred to as anti-e-D-monomer/e-D-dimer antibodies) were screened by the ELISA method as mentioned below.

(c) Establishment of Hybridomas

The presence of produced antibodies in the supernatant of the hybridoma culture was determined by the ELISA method. Into each well of 96-well ELISA plates (Immulon II; Nippon Dynatech K. K.), the purified e-D-dimer solution obtained in Example 1 (A280 nm=0.05, diluted with physiological saline) was poured in an amount of 50 µl, respectively, and allowed to stand at 25° C. for 2 hours. Thereafter, the wells were washed three times with 0.05% Tween 20/physiological saline. Then, 50 µl of the supernatant of the hybridoma culture was added to each well and a reaction was carried out at 25° C. for 1 hour.

Then, 50 µl of a peroxidase-conjugated anti-mouse antibody (Dako Co., Denmark) diluted 200-fold with 0.05% Tween 20/physiological saline was added to each well. After the reaction was completed, the wells were washed three times with 0.05% Tween 20/physiological saline. Thereafter, 250 µl of a solution containing 0.5 mM aminoantipyrine, 10 mM phenol, and 0.005% hydrogen peroxide was added to each well, and a reaction was carried out at 25° C. for 30 minutes. Then, the absorption at 490 nm of each well was measured. As a result, antibody production was observed in 12 wells of the 192 wells.

The anti-e-D-dimer antibodies in the culture supernatants selected by the above ELISA method were examined for the reactivities to e-D-monomer, e-fragment X, e-fragment Y, e-fragment E, and fibrinogen, using 96-well ELISA plates sensitized with the antigens in the same manner. The rest results showed that, of 12 well-culture supernatants which reacted with e-D-dimer, one well-culture supernatant reacted with e-D-monomer, but did not react with e-fragment X, e-fragment Y, e-fragment E, or fibrinogen, whereas the remaining eleven well-culture supernatants did not react with e-fragment E, but reacted with e-D-monomer, e-fragment X, e-fragment Y, and fibrinogen.

The hybridomas in the well supernatant specifically reactive to the e-D-dimer and the e-D-monomer were transferred to a 24-well plate and were cultivated for 4 to 5 days in an HT medium containing 10 to 15% fetal calf serum. Thereafter, the cross reactivities with digestion products of fibrinogen with plasmin (a mixture of p-fragment X, p-fragment Y, p-fragment D and p-fragment E) and digestion product of the stabilized fibrin with plasmin (p-DD/E complex) were determined by the ELISA method, to find no cross reaction with plasmin-digested products. Further, the presence of the produced anti-e-D-monomer/e-D-dimer antibodies was confirmed by the ELISA method, and then, cloning was carried out by the limiting dilution method. In the limiting dilution method, 100 µl of the cell suspension diluted with an HT medium so that the concentration of the hybridoma became 5 hybridomas/ml was poured into each of the wells of 96-well plate wherein $2 \times 10^4$ abdominal cells of normal BALB/C mice were poured in advance in each well. After about 10 days, clones of the hybridomas producing anti-e-D-dimer and anti-e-D-monomer antibodies were screened by the ELISA method. As a result, 20 clones producing antibodies were obtained. From these clones, stable ones exhibiting strong proliferation and a high ability for secreting antibodies were selected, and recloned by the same method as above, and hybridoma IF-101 producing anti-e-D-monomer/e-D-dimer antibodies was obtained. The above hybridoma was domestically deposited in the National Institute of Bioscience and Human-Technology Agency of Industrial Science and Technology Agency of Industrial Science and Technology (Address: 1-3, Higashi 1-chome, Tsukuba-shi, Ibaraki-ken 305, Japan) on Apr. 24, 1996, under FERM P-15599, and was transferred to international deposition on Mar. 31, 1997. The international deposition number is FERM BP-5890.

Example 3

Preparation of Monoclonal Antibody (a) In Vitro Method

Mouse hybridoma IF-101 was cultivated in a DME medium containing 15% fetal calf serum at 37 ° C. for 72 to 96 hours in a 5% carbon dioxide atmosphere. After the culture was centrifuged (10,000×g, 10 minutes), solid ammonium sulfate was gradually added to the supernatant so that a final concentration thereof became 50%. The mixture was stirred for 30 minutes while cooled with ice. After allowed to stand for 60 minutes, the mixture was centrifuged (10,000×g, 10 minutes). The residue was dissolved in a small amount of a 10 mM phosphate buffer (pH 8.0) and was dialyzed to a 1000-fold amount of 10 mM phosphate buffer. The resulting dialyzate was applied to a column of DEAE-cellulose which had been equilibrated with 10 mM phosphate buffer. The monoclonal antibody was eluted by the density gradient method between 10 mM phosphate buffer (pH 8.0) to 10 mM phosphate buffer (pH 8.0) containing 0.2 M NaCl. The eluted monoclonal antibody was concentrated by the ultra filtration method and was dialyzed to 0.1 M phosphate buffer (pH 8.0). To remove the bovine serum IgG, the dialyzed product was passed through goat anti-bovine serum IgG-Sepharose 4B column. Then, the passed solution was applied to a protein A-Sepharose 4B column equilibrated with 0.1 M phosphate buffer (pH 8.0). The column was eluted with a buffer (pH 3.5) to obtain the purified anti-e-D-monomer/e-D-dimer monoclonal antibody IF-101 according to the present invention.

(b) In Vivo Method

Bristane (2,6,10,14-tetramethylpentadecane) (0.5 ml) was administered intraperitoneally into 10 to 12 week old BALB/C mice. After 14 to 20 days, the abdominal cavities of the mice was inoculated with $2 \times 10^6$ cells/mouse of hybridoma IF-101 proliferated in vitro.

About 10 to 15 ml of ascites was obtained from a mouse. The concentrations of the antibody were 5 to 10 mg/ml. The purification of the monoclonal antibody from ascites was carried out by repeating the procedures same as those in vitro purification, except that the step of passing through a column of goat anti-bovine serum IgG-Sepharose was not carried out.

Example 4

Determination of Immunoglobulin Class and Specificity of Monoclonal Antibody

The immunoglobulin class of the anti-e-D-monomer/e-D-dimer monoclonal antibody IF-101 of the present invention was examined by the Ouchterlony immunodiffusion method. The immunoglobulin class of the monoclonal antibody IF-101 was IgG1κ.

Example 5

Determination of sites recognized by the monoclonal antibody

The recognition site of the monoclonal antibody IF-101 was identified by a western blotting method. The procedures were mainly in accordance with the Zeta-Probe Blotting Mewbranes Instruction Manual (Bio-Rad, USA), as follows: Fibrinogen was treated with granulocyte elastase for 30 minutes, 60 minutes or 24 hours. The digested fibrinogen-products after the reaction for 30 minutes, 60 minutes and 24 hours were treated by an SDS polyacrylamide gel electrophoresis in the presence or absence of dithiothreitol (DTT). Blotting and enzyme immunoassay were carried out in the above method. The results therefrom and the results from protein staining of the above SDS polyacrylamide gel electrophoresis with Coomassie Brilliant Blue G-250 were compared to identify the recognition site of the monoclonal antibody IF-101. For fibrinogen, purified e-D-dimer and e-DD/E complex (digestion products of stabilized fibrin with granulocyte elastase), the same procedures were repeated. The binding reactivities of the present monoclonal antibody IF-101 to various antigens are shown in Table 1. In Table 1, "+" denotes that the monoclonal antibody exhibited binding reactivity, and "−" denotes that the monoclonal antibody did not exhibit binding reactivity.

TABLE 1

| Antigens | Binding reactivity |
| --- | --- |
| Fibrinogen | − |
| e-x | − |
| e-Y | − |
| e-D | + |
| e-E1 | − |
| e-E2 | − |
| e-E3 | − |
| e-D-dimer | + |
| e-DD/E complex | + |
| Aα | − |
| Bβ | − |
| γ | − |
| e-D-monomer/α | + |
| e-D-monomer/β | − |
| e-D-monomer/γ | − |

Further, for digested fragments X, Y, D, and E of fibrinogen with plasmin, p-D-dimer and p-DD/E complex (digestion products of stabilized fibrin with plasmin), the same procedures were repeated. The results are shown in Table 2.

TABLE 2

| Antigens | Binding reactivity |
| --- | --- |
| Fibrinogen | − |
| p-x | − |
| p-Y | − |
| p-D | − |
| p-E1 | − |
| p-E2 | − |
| p-E3 | − |
| p-D-dimer | − |
| p-DD/E complex | − |
| Aα | − |
| Bβ | − |
| γ | − |
| p-D-monomer/α | − |
| p-D-monomer/β | − |
| p-D-monomer/γ | − |

As above, the results of Tables 1 and 2 show that the monoclonal antibody IF-101 of the present invention recognizes the /α chain of e-D-monomer.

Example 6

Identification of Epitope of Monoclonal Antibody IF-101

The results of Example 5 show that the monoclonal antibody IF-101 recognizes the /α chain of e-D-monomer. Thus, to analyze the epitope of the monoclonal antibody IF-101 in detail, the amino acid sequence of the /α chain of e-D-monomer was determined. Then, peptides having the same amino acid sequences were prepared, and binding-inhibiting experiments between the monoclonal antibody IF-101 and e-D-monomer, e-D-monomer/α chain, e-D-dimer, and e-DD/E complex were carried out, using the peptides, to determine the amino acid sequence of the epitope. Concrete procedure is as follows:

The amino acid sequence at the N-terminus of the /α chain of e-D-monomer was analyzed by a protein sequencer (Applied Systems Japan K.K.) to find Ser Glu Asp Leu Arg Ser Arg Ile (SEQ ID NO: 2).

A comparison of the found sequence as above and the sequence of the Aα chain of human fibrinogen revealed that the /α chain of e-D-monomer begins with the 112nd amino acid of the Aα chain. In other words, it was found that the N-terminal amino acid sequence including the N-terminus amino acid of the /α chain of e-D-monomer corresponds to $Ser_{112}$-$Glu_{113}$-$Asp_{114}$-$Leu_{115}$-$Arg_{116}$-$Ser_{117}$-$Arg_{118}$-$Ile_{119}$- of the Aα chain of human fibrinogen.

Three peptides having amino acid sequences after the 112nd amino acid of the Aα chain of human fibrinogen were prepared. The binding-inhibiting experiments between the monoclonal antibody IF-101 and e-D-monomer, e-D-monomer/α chain, e-D-dimer, and e-DD/E complex (digestion product of stabilized fibrin with granulocyte elastase) were carried out, using the peptides.

The binding-inhibiting experiments were conducted by a western blotting method. More particularly, the products (containing e-D-monomer) obtained by digesting fibrinogen with granulocyte elastase for 24 hours were treated by an SDS polyacrylamide gel electrophoresis, together with the purified e-D-dimer and e-DD/E complex (digestion products of stabilized fibrin with granulocyte elastase), in the presence or absence of dithiothreitol (DTT). Then, blotting was carried out in accordance with the Zeta-Probe Blotting Mewbranes Instruction Manual (Bio-Rad, USA). In the blotting, the monoclonal antibody IF-101 was reacted in the presence of the peptides (100 μM) or the absence thereof, to determine whether or not the peptides inhibit the reaction of the monoclonal antibody IF-101.

The results are shown in Table 3. The peptide A has the amino acid sequence:

Ser Glu Asp Leu Arg Ser (SEQ ID NO: 1), which corresponds to the amino acid sequence from the 112nd to 117th amino acids in the Aα chain of human fibrinogen. The peptide B has the amino acid sequence:

Ser Arg Ile Glu Val Leu (SEQ ID NO: 3), which corresponds to the amino acid sequence from the 117th to 122nd amino acids in the Aα chain of human fibrinogen. The peptide C. has the amino acid sequence:

Leu Lys Arg Lys Val Ile (SEQ ID NO: 4), which corresponds to the amino acid sequence from the 122nd to 127th amino acids in the Aα chain of human fibrinogen. In Table 3, "+" denotes that the binding of the monoclonal antibody IF-101 and the products digested with granulocyte elastase was inhibited by the peptide added, and "−" denotes that the binding was not inhibited by the peptide added.

The results of Table 3 show that the epitope of the monoclonal antibody IF-101 exists at the site containing the N-terminal amino acid sequence, which is the same amino acid sequence as that of peptide A(SEQ ID NO: 1):

Ser-Glu-Asp-Leu-Arg-Ser which contains the N-terminal amino acid of the /α chain of e-D-monomer. The amino acid sequence corresponds to:

$Ser_{112}$-$Glu_{113}$-$Asp_{114}$-$Leu_{115}$-$Arg_{116}$-$Ser_{117}$-$Arg_{118}$-$Ile_{119}$- of the Aα chain of human fibrinogen.

TABLE 3

|  | e-D-monomer | e-D-monomer/α | e-D-dimer | e-DD/E complex |
|---|---|---|---|---|
| Peptide A | + | + | + | + |
| Peptide B | − | − | − | − |
| Peptide C | − | − | − | − |

Example 7

Preparation of Monoclonal Antibody IF-101-bound-latex, and Determination of e-D-Dimer and e-DD/E Complex (Digestion Products of Stabilized Fibrin with Granulocyte Elastase, Using the Latex Polystyrene latex [Seradyn; USA, 10% (w/v) suspension, particle diameter=0.489 μM] (0.2 ml) was mixed with 1.8 ml of 50 mM tris-HCl buffer (pH 8.0) (antibody concentration =0.9 mg/ml) containing the anti-e-D-monomer/e-DD/E complex monoclonal antibody IF-101 prepared in Example 3 in accordance with the present invention, and the mixture was stirred with a magnetic stirrer.

The mixture was centrifuged (20,000×g; 10 minutes), washed with distilled water containing 0.05% $NaN_3$ four times, suspended in 0.1 M tris-HCl buffer (pH 8.0) containing BSA (1 mg/ml) and stored. The coated latex was mixed with various concentrations of e-D-dimer, e-DD/E complex, digestion products of fibrinogen with granulocyte elastase, digestion products of fibrinogen with plasmin, or digestion products of stabilized fibrin with plasmin. A fully-automatic immunological serum testing system (LPIA-200; Mitsubishi Chemical Corp.) was used to measure the reaction rates of agglutination for determination.

The results are shown in FIG. 1. In FIG. 1, the line a illustrates the results of e-D-dimer used as an antigen, the line b illustrates the results of e-DD/E complex, the line c illustrates the results of a mixture of e-DD/E complex and p-DD/E complex in equivalent amounts, the line d illustrates the results of the digestion products of fibrinogen with plasmin, the line e illustrates the results of p-DD/E complex, and the line f illustrates the results of the digestion products of fibrinogen with granulocyte elastase. The V value means a reaction rate of agglutination.

The results of Table 1 show that e-D-dimer or e-DD/E complex can be quantitatively measured by the latex coated with monoclonal antibody IF-101.

Industrial Applicability

As above, it is manifest that the monoclonal antibody of the present invention can provide an immunological assay capable of quantitatively and specifically determining an amount of e-D-dimer or e-DD/E complex in a sample from a living body, without interference of the substances which are supposed to be present in the sample, i.e., fibrinogen, digestion products of fibrinogen with plasmin, or digestion products of stabilized fibrin with plasmin, particularly p-D-dimer or p-DD/E complex.

As above, the present invention was explained with reference to particular embodiments, but modifications and improvements obvious to those skilled in the art are included in the scope of the present invention.

What is claimed is:

1. A monoclonal antibody which specifically reacts with D-monomer produced by digesting human fibrinogen with granulocyte elastase and D-domain containing digestion products produced by digesting human stabilized fibrin with granulocyte elastase, but does not react with fibrinogen, or does not react with fragment X, Y or E produced by digesting fibrinogen with granulocyte elastase.

2. The monoclonal antibody according to claim 1, which does not react with digestion products of human fibrinogen with plasmin, or digestion products of stabilized fibrin with plasmin.

3. An antibody fragment of said monoclonal antibody according to claim 1 or 2, which contains an antigen-binding site specifically reacting with D-monomer produced by digesting human fibrinogen with granulocyte elastase and D-domain containing digestion products produced by digesting human stabilized fibrin with granulocyte elastase.

4. A hybridoma which produces said monoclonal antibody according to claim 1 or 2.

5. A monoclonal antibody which reacts with a peptide having an amino acid sequence, SEQ ID NO: 1:

Ser Glu Asp Leu Arg Ser.

6. An antibody fragment of said monoclonal antibody according to claim 5, which contains an antigen-binding site reacting with said peptide having said amino acid sequence, SEQ ID NO: 1.

7. A hybridoma which produces said monoclonal antibody according to claim 5.

8. An immunological assay for D-dimer produced by digesting human stabilized fibrin with granulocyte elastase and DD/E complex produced by digesting human fibrin with granulocyte elastase, in a sample from a living body, characterized by bringing said sample into contact with a carrier coated with the monoclonal antibody according to claim 1 or 2, the monoclonal antibody according to claim 5, or the antibody fragment according to claim 6, and detecting aggregate formed by said D-dimer or DD/E complex with said coated carrier.

9. An immunological assay for D-dimer produced by digesting human stabilized fibrin with granulocyte elastase and DD/E complex produced by digesting human fibrin with granulocyte elastase, in a sample from a living body, characterized by bringing said sample into contact with a carrier coated with the antibody fragment according to claim 3 and detecting aggregate formed by said D-dimer or DD/E complex with said coated carrier.

* * * * *

UNITED STATES PATENT AND TRADEMARK OFFICE
CERTIFICATE OF CORRECTION

PATENT NO. : 6,132,719
DATED : October 17, 2000
INVENTOR(S) : Isao Kohno, et. al.

It is certified that error appears in the above-identified patent and that said Letters Patent is hereby corrected as shown below:

In claim 8, line 39 after "human" insert --stabilized--.

In claim 9, line 49 after "human" insert --stabilized--.

Signed and Sealed this

Twenty-second Day of May, 2001

*Attest:*

NICHOLAS P. GODICI

*Attesting Officer*     *Acting Director of the United States Patent and Trademark Office*

SEQUENCE LISTING

<160> NUMBER OF SEQ ID NOS: 4

<210> SEQ ID NO 1
<211> LENGTH: 6
<212> TYPE: PRT
<213> ORGANISM: Homo sapiens

<400> SEQUENCE: 1

Ser Glu Asp Leu Arg Ser
 1               5

-continued

```
<210> SEQ ID NO 2
<211> LENGTH: 8
<212> TYPE: PRT
<213> ORGANISM: Homo sapiens

<400> SEQUENCE: 2

Ser Glu Asp Leu Arg Ser Arg Ile
 1               5

<210> SEQ ID NO 3
<211> LENGTH: 6
<212> TYPE: PRT
<213> ORGANISM: Homo sapiens

<400> SEQUENCE: 3

Ser Arg Ile Glu Val Leu
 1               5

<210> SEQ ID NO 4
<211> LENGTH: 6
<212> TYPE: PRT
<213> ORGANISM: Homo sapiens

<400> SEQUENCE: 4

Leu Lys Arg Lys Val Ile
 1               5
```